United States Patent
Titcombe et al.

(10) Patent No.: US 12,337,322 B2
(45) Date of Patent: Jun. 24, 2025

(54) CASSETTE ASSEMBLY AND PROCESSING METHOD

(71) Applicant: CellPath Ltd, Powys (GB)

(72) Inventors: Richard Titcombe, Powys (GB); Philip Webber, Powys (GB); Paul Webber, Powys (GB)

(73) Assignee: CellPath Ltd, Powys (GB)

( * ) Notice: Subject to any disclaimer, the term of this patent is extended or adjusted under 35 U.S.C. 154(b) by 707 days.

(21) Appl. No.: 17/497,530

(22) Filed: Oct. 8, 2021

(65) Prior Publication Data
US 2022/0134330 A1 May 5, 2022

(30) Foreign Application Priority Data
Oct. 12, 2020 (GB) ..................................... 2016155

(51) Int. Cl.
*B01L 1/00* (2006.01)
*B01L 3/00* (2006.01)

(52) U.S. Cl.
CPC ....... *B01L 3/5055* (2013.01); *B01L 2200/025* (2013.01); *B01L 2200/141* (2013.01); *B01L 2300/021* (2013.01); *B01L 2300/043* (2013.01); *B01L 2300/0609* (2013.01); *B01L 2300/123* (2013.01)

(58) Field of Classification Search
CPC ............ B01L 3/5055; B01L 2200/025; B01L 2200/141; B01L 2300/021; B01L 2300/043; B01L 2300/0609; B01L 2300/123; B01L 2300/0819; B01L 9/52; B01L 3/545; A61B 10/0096; G01N 1/31; G01N 1/36; G01N 1/312; G01N 2001/315
See application file for complete search history.

(56) References Cited

U.S. PATENT DOCUMENTS

| | | | |
|---|---|---|---|
| 3,674,396 A | 7/1972 | McCormick | |
| 6,207,408 B1* | 3/2001 | Essenfeld | ............. G01N 1/312 435/40.52 |
| 9,594,087 B2 | 3/2017 | Webber et al. | |
| 9,810,611 B2 | 11/2017 | Webber et al. | |
| 10,288,536 B2 | 5/2019 | Webber et al. | |

(Continued)

FOREIGN PATENT DOCUMENTS

| | | |
|---|---|---|
| GB | 1230913 A | 5/1971 |
| GB | 2278441 A | 11/1994 |

(Continued)

OTHER PUBLICATIONS

Search Report under Section 17(5) for Application No. GB2016155.0 dated Mar. 18, 2021.

*Primary Examiner* — Jyoti Nagpaul
(74) *Attorney, Agent, or Firm* — Cook Alex Ltd.

(57) ABSTRACT

A histology processing assembly comprising a frame with an area for application of a unique identifier for a biological sample and a recess for irreversibly receiving a sample carrier which has a compartment for holding the sample which is transmissible to processing fluids. A method is provided in which the sample is placed in the carrier with identifying information at a first location and transported to a second location and loaded into a carrier, marked with the identifying information. The carrier may be used to hold the sample in a pre-determined orientation for processing.

18 Claims, 12 Drawing Sheets

(56) References Cited

U.S. PATENT DOCUMENTS

2005/0147538 A1* 7/2005 Williamson ............ B01L 3/508
422/400
2014/0273084 A1* 9/2014 Boehl ...................... G01N 1/36
435/40.52

FOREIGN PATENT DOCUMENTS

| GB | 2453320 A * | 4/2009 | ............ G01N 1/36 |
|----|-------------|--------|-----------------------|
| WO | 2005037182 A2 | 4/2005 | |
| WO | 2009055592 A1 | 4/2009 | |
| WO | 2009055595 A1 | 4/2009 | |
| WO | 2011133453 A2 | 10/2011 | |

* cited by examiner

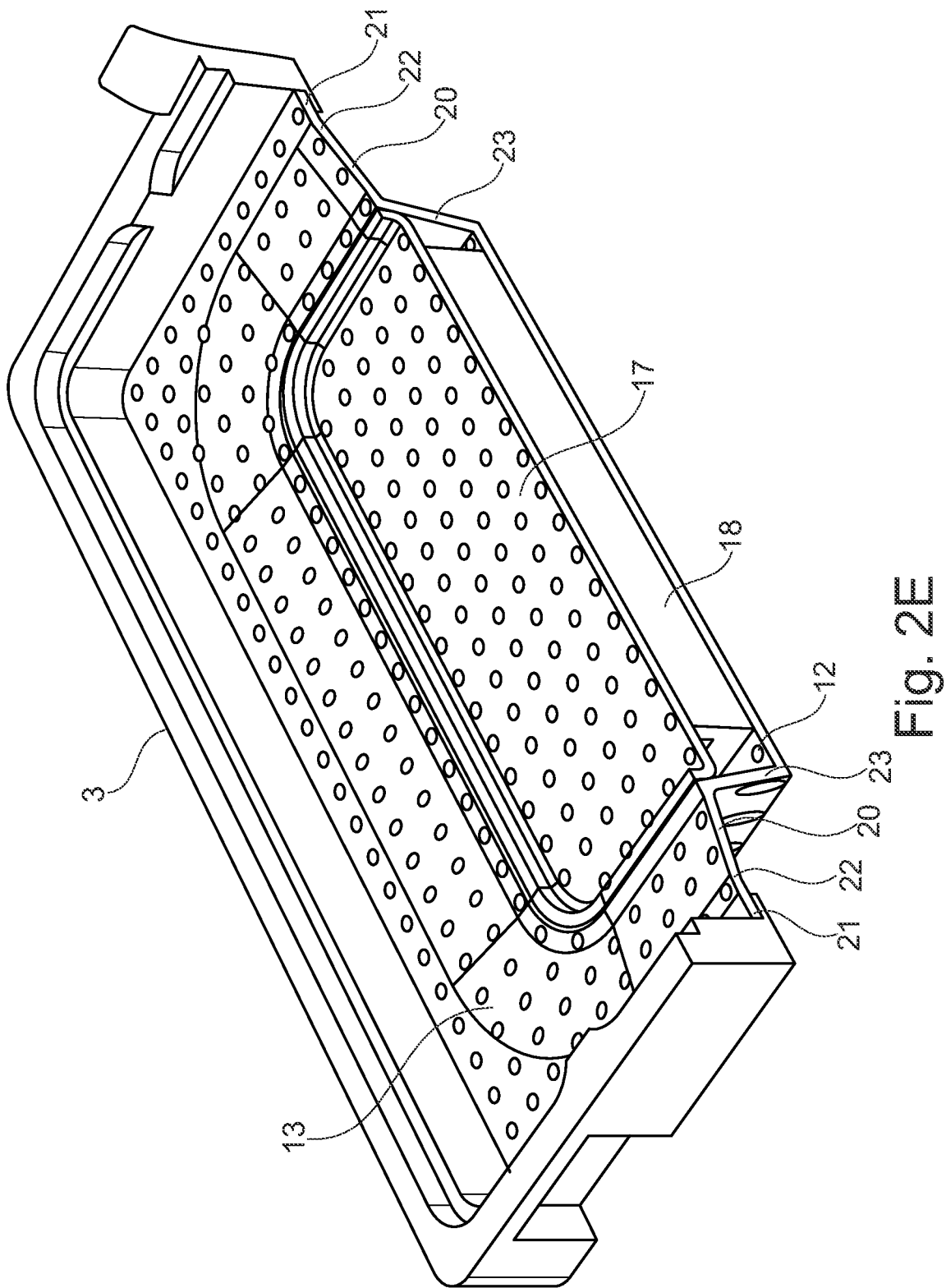

CASSETTE ASSEMBLY AND PROCESSING METHOD

CROSS REFERENCE TO RELATED APPLICATION

This application claims the benefit of and priority to Great Britain Application No. 2016155.0, filed Oct. 12, 2020, the disclosure of which is hereby incorporated by reference in its entirety.

FIELD OF INVENTION

This invention relates to a cassette assembly, in particular a histology processing cassette assembly suitable for processing a biological tissue sample and to a processing method. The invention relates particularly to a multi-part cassette assembly having a sample carrier and a frame and a method to a method for processing a biological tissue sample in which the sample is placed in the sample carrier before the sample carrier is irreversibly located in the frame. The invention also relates to a method of providing a processing cassette assembly with a unique sample identifier and to such a cassette assembly.

BACKGROUND

Biological materials for histological examination are processed in large quantities for a wide range of diagnostic purposes. It is essential to ensure that tissue samples remain uniquely identified with the source of the tissue for technical, medical, ethical and legal reasons. Typically, the tissue is obtained from its source, which may be a patient or from a stored sample, the tissue is then placed in a sample pot or vial and typically transported or mailed to a location for tissue processing. The sample is typically placed into the pot or vial in a random orientation such that the orientation of the sample when subjected to sectioning will not be determined directly by the medical practitioner taking the sample. Samples may be taken from a patient in any medical establishment such as a clinic, surgery or hospital but tissue processing/sample analysis is typically carried out at a remote location in a laboratory.

Tissue processing conventionally involves placing the sample into a histology processing cassette and treating with processing solutions or fluids depending on the nature of the sample to dehydrate or otherwise treat the tissue sample. Typical fluids employed in such processing may include alcohol such as ethanol, paraffin, xylene, formaldehyde and water. The treated tissue sample is then embedded in paraffin or wax and cooled to provide the sample in a rigid form suitable for thinly slicing the embedded sample using a microtome to provide a section of the sample suitable for analysis. Processing the sample and embedding the tissue in paraffin provides it with the rigidity necessary for further processing, for example microtome slicing. These processing steps involve manual handling by a laboratory technician, exposing the sample to potential damage and also requires the technician to orientate the sample into the appropriate aspect for embedding or setting in the paraffin prior to sectioning.

The sample section is typically subjected to further handling processes and stained, mounted, and subjected to microscopic analysis. Results are then reported and the sample section archived which may be onsite or offsite. Throughout the process from taking the sample sample storage, information about the tissue sample must remain associated with the sample so as to be able to uniquely identify the sample and its source at any point in the process. Typically, a large number of samples, for example 50 or more are processed together.

Known cassettes for processing biological tissues typically comprise an open-topped box with a perforated bottom wall. The box may have a perforated top cover which is moveable relative to the box such as a hinged lid or removable. The cassette typically has three vertical side walls and the fourth, side wall, on the front side of the cassette is typically sloping and includes an area for labelling the cassette. Labelling the cassette links the sample in the cassette to its source via a record, which may be kept manually or electronically. Processing cassettes may define one cavity and process one sample at a time or may have multiple cavities to allow processing of multiple samples. Processing cassettes are typically constructed of plastics material and the perforations are made in the plastic material which forms the bottom wall and, where employed, the plastics material forming the lid. In other embodiments, a fine mesh may be employed in the base and or lid to allow passage of fluids therethrough while the sample is being prepared or embedded. The perforations of the cassette are typically from 1 to 3 mm in diameter. Known processing cassettes are described for example in GB 1230913 and U.S. Pat. No. 3,674,396.

Certain samples may be very small in size and may pass through perforations in conventional cassettes. Various approaches have been adopted to enable small specimens to be processed in standard processing cassettes including using an insert or adaptor for holding one or more samples which may be inserted into a histology processing cassette. GB-A-2278441 describes an adaptor for insertion into a histology processing cassette to enable the cassette to be used for processing small tissue specimens. The adaptor suitably fits within a processing cassette and comprises a base and a lid to engage the base and define therewith a chamber to hold a tissue sample with one of the base and the lid comprising a peripheral frame across which a fine mesh is disposed. The adapter is then placed in the cassette and may be retained in the cassette by fitting a lid to the cassette. The adapter is not engaged with or retained in a fixed relation to the cassette.

We have now devised a novel histology processing assembly that enables a biological sample to be obtained from a source and subjected to a sample processing procedure with improved sample tracking, ensuring the orientation of the sample is determined by the medical professional taking the sample and reducing the risk of sample damage by reducing need for sample manipulation during processing.

SUMMARY

In a first aspect, the invention provides a histology processing assembly comprising
  i) a cassette frame comprising a recess for irreversibly receiving a sample carrier; and
  ii) a sample carrier comprising a compartment for holding a biological sample, the sample carrier being adapted for irreversible engagement with the said cassette frame.

Advantageously, the histology processing assembly allows a sample to be taken from a patient, archive or other source and placed in a sample carrier at a first location and transported to a second location for processing. Handling of the sample is minimised and the risk of damage to the sample by repeated handling is reduced.

The clinician or technician obtaining the sample is able to place the sample in the sample carrier in a particular orientation as may be suitable for clinical or analytical purposes to ensure appropriate orientation of the sample during downstream processing, for example sectioning. No further intervention with the sample is necessary or desirable. The clinician may thereby ensure that the sample is appropriately orientated according to clinical need in subsequent processing.

As the sample carrier is irreversibly engaged with the cassette frame, the sample is presented in the desired orientation as intended upon placing the sample in the sample carrier.

The sample is suitably placed in a sample carrier at the first location and placed in a receptacle, for example a sample pot or vial to which a unique identifier or sample data may be applied. At the second location, the unique identifier or sample data is suitably applied to the frame and the carrier is irreversibly placed in the frame, thereby ensuring the assembly is uniquely marked and tracked so as to provide complete traceability and identification of the sample and its origin. The sample may then be subjected to standard histology processing. The assembly reduces the need to handle the sample at the second location as it is being prepared for processing.

In a second aspect, the invention provides a method of handling a biological sample preparatory to a histology processing procedure comprising:
 i) placing a biological sample in a sample carrier comprising a compartment for holding a biological sample at a first location;
 ii) placing the sample carrier in a receptacle and, preferably, recording data comprising a unique identifier associated with the sample on the receptacle;
 iii) transporting the receptacle to a second location;
 iv) removing the sample carrier from the receptacle and irreversibly locating the sample carrier containing the biological sample in the cassette frame to provide a histology processing assembly comprising the cassette frame and the sample carrier which contains the sample.

The method preferably comprises the step of applying a unique identifier for the biological sample to the receptacle at the time the sample carrier is placed therein and the step of applying the unique identifier for the sample to the cassette frame such that upon irreversibly inserting the sample carrier in the cassette frame, the biological sample may be uniquely identified from the unique identifier on the cassette frame.

The sample may then be subjected to a histology processing procedure on the sample to provide analytical results or data while the sample is associated with its unique identifier.

The method also reduces the risk of damage to the sample inherent in multiple handling in known processes where the sample is first handled and placed in a pot for transportation to a processing location and then further handled by manually removing the sample from the pot and placing it in a processing cassette. The invention advantageously enables very fine or delicate samples to be processed in a histology processing procedure.

The cassette frame of the histology processing assembly suitably comprises three vertical side walls and a fourth, sloping, side wall, on the front side of the cassette frame, together defining a recess for irreversibly receiving the sample carrier. The cassette frame suitably comprises an area for application of the unique identifier, preferably the sloping wall.

The top face and/or the bottom face of the cassette frame are transmissible to processing fluids and/or radiation. The top face and/or bottom face may be open without any form of covering or may comprise a covering. The covering may comprise any arrangement through which processing fluids and/or radiation may pass and preferably comprises a wall, for example a rigid plastic wall, having apertures formed therein, or a covering, for example a mesh covering or a flexible plastics covering having apertures formed therein, transmissible to histology processing fluids. The apertures may be of any suitable shape, for example, circular, hexagon, and square. The apertures in the top and/or bottom face may be arranged in any pattern and is preferably a regular pattern presenting an array of apertures to maximise transmissibility of processing fluids.

Suitably, the external size, shape and configuration of the cassette frame is in the same or a substantially similar form to a known histology processing cassette. The cassette frame may comprise locating means such that the sample carrier or a bottom part and/or top apart of the sample carrier, upon location in the frame, is held in a fixed relationship to the cassette frame, preferably in a snug-fitting arrangement. The locating means may comprise a peripheral lip extending inwardly from the side walls such that the sample carrier rests on the lip upon insertion to the frame or may comprise a bottom face on which the sample carrier may rest upon placement in the frame.

Suitably, the sample carrier fits in the cassette frame snugly, preferably the outside face of the frame is adjacent to the inside face of the cassette frame. The sample carrier and/or cassette frame may comprise engagement means such that the sample carrier clips into the cassette frame and especially, engages irreversibly with the cassette frame such that the sample carrier may not be removed from the cassette frame in tact.

The cassette frame is suitably constructed of rigid plastics material.

The cassette frame is suitably the same size and dimensions as a histology processing cassette. Histology cassettes are generally of a "standard size" as it is required to fit in other apparatus, for example fit standard specimen holders of microtomes and in printing equipment, employed to label each cassette with information typically relating to the sample in the cassette for example, the patient from whom the sample has been taken. "standard size" histology processing cassettes. Minor variations in size may occur, dependent for example upon the wall thickness of the box. Whilst standard size cassettes may be employed for the majority of tissue samples, certain samples, for example prostate samples are larger than the standard size cassette and require a larger cassette. Larger cassettes typically have an area four times that of a standard cassette and a depth of around twice that of a standard cassette.

Preferably, the cassette frame has internal dimensions of 28 to 32 mm×25 to 28 mm×5 to 10 mm, similar to the dimensions of a "standard size" histology cassette or internal dimensions of around 50 to 55 by 65 to 80 by 12 to 17 mm, similar to the dimensions of a known "larger size" histology cassettes. The cassette frame may have a similar length and width to a larger size histological cassette but a depth similar to a standard size cassette, preferably to 55 by 65 to 80 by 6 to 9 mmmm, as disclosed in EP-A-2851672.

The cassette frame may comprise a pivotally mounted lid which is hingedly mounted to one of the peripheral walls and closable. Alternatively, a separate lid engagable with the peripheral wall of the cassette frame to close the compartment may be provided.

In a preferred embodiment, the sample carrier and cassette frame are dimensioned such that the top face of the sample carrier is flush with the plane defined by the top edge of the cassette frame when the sample carrier is irreversibly located in the cassette frame. one embodiment.

The cassette frame may comprise an aperture passing vertically through a wall of the cassette frame for receiving a connecting strip in a direction perpendicular to the plane of the cassette. The aperture may pass vertically through a side wall, end wall or preferably the front wall of the frame. The aperture allows a connecting strip to be passed therethrough such that a plurality of frames may be threaded onto the strip such that they may be held in register, for example as described in EP-A-2913655.

The area for application of the unique identifier is suitably the front sloping wall of the frame. The frame may be marked using a machine which imparts a unique identifier, for example a 2-dimensional bar-code, on the front wall of the cassette for ease of observation.

The cassette frame is adapted to receive a unique identifier applied to an area of the frame, preferably a front sloping wall, for ease of observation by a technician in use. The unique identifier may be applied manually or, preferably, automatically, for example using a cassette printer or labelling device. The marking is suitably indelibly applied to the cassette for example by printing onto or etching into the material from which the frame is constructed. Automated labelling devices enable rapid throughput and application of a unique identifier or data from electronically stored patient records, for example from a Laboratory Information Management System. Devices for applying a unique identifier to a cassette and may be adapted to receive the frame for printing.

The sample carrier defines a sample compartment for carrying one or more samples, preferably in discrete cavities. The sample carrier suitably includes a closable lid such that the sample(s) may be placed in the sample compartment and the lid then closed such that the sample compartment is closed. Preferably the sample compartment is dimensioned so as to hold the sample in a fixed position upon insertion of the sample into the sample compartment and on closing the sample carrier.

The sample carrier comprises a rigid frame. The rigid frame suitably comprises locating or engagement means to allow the rigid frame of the sample carrier and the cassette frame to be irreversibly engaged together.

The rigid frame of the sample carrier is preferably constructed of rigid plastics material, configured for insertion into and irreversible engagement with the cassette frame. The rigid frame of the sample carrier is preferably a square or rectangular and dimensioned to fit within the cassette frame and to be irreversibly engagable therewith.

The rigid frame of the sample carrier may comprise a single part defining the rigid frame or comprise an upper part and a lower part adapted to engage together to form the rigid frame.

The sample carrier further comprises a bottom face and a top face each having apertures therein which are transmissible to a histology processing fluid and/or radiation. The bottom part and the top part are securable together to define an enclosed sample compartment.

The bottom face and top face of the sample carrier may comprise a rigid or flexible sheet. In one embodiment the top face and/or bottom face comprise a plastic molded sheet having apertures defined therein. The apertures may be of any suitable shape, for example, circular, hexagon, and square. The apertures in the top and/or bottom face may be arranged in any pattern and is preferably a regular pattern presenting an array of apertures to maximise transmissibility of processing fluids.

In another embodiment, the top face and/or bottom face may comprise a mesh covering or a flexible plastics covering, having apertures formed therein transmissible to processing liquids and/or radiation for analysis.

Preferably the top face and the bottom face comprise a fine mesh secured to the rigid frame to define a sample compartment. Preferably, the mesh has a pore size of no more than 1 mm and more preferably of no more than 500 microns. More typically, the pore size is from 40 to 400 microns. Preferably, the mesh is made of polyamide (nylon).

In one embodiment, the lower part comprises a bottom peripheral frame and a bottom face material within the bottom peripheral frame and the upper part comprises a top peripheral frame and a top face material within the top peripheral frame. In one embodiment, the lower part comprises the peripheral rigid wall and the upper part comprises a lid, preferably a planar lid which may be detachable from the bottom part or pivotally mounted thereto. In another embodiment, the lower part comprises the lower part of the peripheral rigid wall and the lower face and the top part comprises the upper part of the peripheral wall and the top face. The bottom face and top face each comprise a mesh or each comprise a rigid plastics sheet having apertures therein.

In a preferred embodiment, the sample carrier comprises a rigid frame defining the rigid wall and a sample compartment. The sample compartment may be defined by the rigid frame of the sample carrier or may comprise a self-contained sample compartment connected to the rigid frame of the sample carrier by a flexible portion, preferably a peripherally-extending flexible portion.

In a preferred embodiment, the sample compartment comprises a flexible bottom part, preferably square or rectangular, defining a depression into which the sample may be placed, and a top closure part which is placed on top of the bottom part to form an enclosed sample compartment within the rigid frame of the sample carrier. The sample compartment is suitably connected to the rigid frame by a peripherally extending flexible portion. Suitably, the self-contained sample compartment is dimensioned so as to be contained between the planes defined respectively by the top edge and the bottom edge of the sample carrier rigid frame in one configuration and to be displaceable to a position proud of either of the said planes in a second configuration.

The flexible portion is suitably located around at least part, and preferably all, of the periphery of the sample compartment and acts as a bridge between the sample compartment and the rigid frame of the sample carrier.

In one embodiment, the flexible portion is configured so as to allow the sample compartment to be located in two stable positions by displacement in a direction perpendicular to the plane of the rigid frame, preferably, in a first stable position, the sample compartment is located wholly within the walls of the cassette frame when the sample carrier is engaged therein and, upon application of force, is movable to a second stable position, such that a part or the entire sample compartment extends above or below a plane defined respectively by the top of the walls of the cassette frame and by the bottom of the walls of the cassette frame.

In one embodiment, the flexible portion comprises an outer part which connects to the rigid frame and an inner part which connects to and extends to the sample compartment.

Together, the inner part and outer part form a bridge between the sample compartment and the rigid frame. Preferably, the inner part, the outer part and preferably both the inner part and the outer part of the flexible portion extend around the sample compartment and thereby engage with a substantial part of the rigid frame.

The inner part and outer part are preferably hingedly connected such that the inner part extends at an inclined angle relative to the plane of the rigid frame in a first configuration and at an inclined angle on the opposite side of the plane in a second configuration. This arrangement enables the sample compartment to be located in a stable first and second position by application of force to displace the sample compartment perpendicularly relative to the plane of the rigid frame with the sample compartment passing through the plane of the rigid frame at which location release of the force applied to the sample compartment will cause the sample compartment to be urged to the first or second position.

The sample compartment and flexible portion suitably comprise apertures to allow the transmission of processing fluids and/or radiation. The apertures also aid deformation of the flexible portion between the first and second position.

Where the upper and/or lower part of the sample carrier comprise a mesh upper and/or lower face, the rigid frame or upper and lower parts forming the rigid frame of the sample carrier are suitably made by injection moulding a thermoplastics material around a mesh such that a peripheral edge portion of the mesh is embedded in the moulded frame.

The sample may be placed directly into the sample compartment of the sample carrier or may be placed in another sample compartment which may be deformable or flexible and which sample compartment is then placed in the sample compartment of the sample carrier.

The sample carrier is dimensioned to fit within the cassette frame and to be irreversibly engagable therewith to ensure the sample and its unique identifier are not separated during processing. Suitably, the external length and/or breadth of the sample carrier are substantially the same as the corresponding internal dimension of the cassette frame. Preferably the external length and breadth of the sample carrier are substantially the same as the internal length and breadth of the cassette frame.

Suitably, the sample compartment is constructed of a material that may be sectioned using a conventional microtome. Preferably, the sample compartment is constructed of a membrane or plastics material The cassette frame and sample carrier are adapted to engage irreversibly upon locating the sample carrier in the cassette frame. Preferably, the sample carrier and cassette frame are irreversibly engaged on insertion of the sample carrier into the cassette frame. The cassette frame and/or sample carrier comprise engaging means such that, upon insertion of the sample carrier into the frame, the sample carrier is engaged, preferably irreversibly engaged, in the cassette frame. As the sample is suitably in an orientation in the sample carrier determined by the clinician or technician taking the sample, and the sample carrier is in a fixed orientation within the cassette frame, the sample is fixed in the orientation intended by the clinician or technician.

The cassette frame suitably comprises engaging means for engagement with the sample carrier. The sample carrier may also comprise complementary engaging means. The engaging means on the cassette frame and sample carrier suitably comprise a lug and a recess. In one embodiment, the frame comprises lugs engagable with the sample carrier and in another embodiment, the sample carrier comprises lugs engagable with the frame. The lug may comprise a projection and be engagable with complementary formation on the other part, respectively the sample carrier or cassette frame, or a larger part, for example a flange or part of the periphery of the sample carrier may engage with the frame or vice versa. The sample carrier and cassette frame are suitably engagable manually.

In one embodiment, the frame and the sample carrier are constructed of plastics material. The engagement means are suitably rigidly deformable to enable manual for example "push fit" or "snap fit" engagement of the sample carrier and the cassette frame.

The compartment of the sample carrier may comprise a single compartment or multiple compartments of any desired shape or configuration. Preferably multiple compartments are disposed in a regular arrangement. Examples of multiple compartments include, lengthways compartments extending along the full length of the sample carrier or widthways compartments extending along the full length of the sample carrier or an array of compartments with two in each dimension, for example the sample compartment may comprise multiple compartments across the width of the compartment and multiple compartments across the length of the compartment, for example a 2×2 array, 2×3, 2×4, 2×5, 3×2, 3×3, 3×4, 3×5 array depending on the type and size of samples to be analysed. The compartments suitably have internal divisions for example partitioning walls. The partitioning walls may extend along the length and/or breadth of the sample carrier. Suitably, any partitioning walls extend from the bottom face to the top face of the compartment to aid sample isolation.

The sample compartment may be configured to receive a separate sample chip. Suitably, the chip is constructed of a deformable material, for example a foam such that upon closure of the sample compartment, the bottom face and top face or lid of the compartment are in contact with and apply a slight force to the chip to compress it and hold it in a fixed relation to the sample carrier. The sample chip may comprise one or more sample bays, the sample chip being sized and adapted for location within the compartment of the sample carrier. The sample chip is preferably planar and fits within the sample compartment such that the plane of the sample and of the sample compartment are parallel or coincident. Suitably, the sample chip comprises a deformable sheet having one or more sample bays formed in one face thereof for receipt of the samples. Preferably, the chip comprises a plurality of sample bays extending along the length of the chip as linear, parallel channels.

Suitable sample chips are available under the trade name BXCHIP available from Lumea. Where multiple compartments are employed, the compartments may be any suitable shape, for example elongate and square and may be arranged in any desired manner in the cassette. Multiple compartments may be defined by one or more partition walls within the compartment defined by the peripheral wall. the partition walls are generally parallel to the internal face of the side walls and in a plane which is preferably generally perpendicular to the bottom face and top face. Suitably the partition walls extend between the top face and the bottom face. Suitably each sample compartment is discrete and contamination or damage of samples from other samples cannot occur or is minimised. Preferably, the compartments are the full vertical depth of the sample carrier, that is the bottom and top face define sides of the compartment. Suitably, the sample carrier contains 2 and preferably at least 3 compartments. Preferably, the compartments are at least 5 mm wide in their smallest dimension parallel to the top or bottom face.

In a preferred embodiment, the sample carrier comprises 2 or 3 lengthways compartments which extend along the length of the sample carrier and are side-by-side.

The compartments may be any suitable shape, for example elongate and square, and may be arranged in any desired manner in the sample carrier. Preferably, the compartments are arranged to extend across the full width of the sample carrier. Endoscopy biopsies for example, may be processed in compartments which are more square than elongate. The shape of the compartment may be relevant in the examination and diagnosis, for example in the examination of a prostate core. A prostate core is generally elongate, for example 20 mm in length and 1 mm in diameter and a cassette having a plurality of elongate channels is preferable in these cases. Elongate channels are preferable for biopsies using needle-shaped cores. In an especially preferred embodiment, the cassette has five identical channel-shaped compartments running across the width of the cassette.

The orientation of a sample during processing and sectioning may be important. As the medic acquires the tissue sample, the medic may require a certain cross-section or aspect of the sample to be presented for examination or observation during processing. We have found that by providing a sample carrier which is dimensioned such that the top face and bottom face hold the sample in place upon closure of the compartment, the orientation of the sample may be set by the medic rather than by the technician to ensure the appropriate aspect of the sample will be sectioned.

In a third aspect, the invention provides a histology processing assembly comprising
  i) a frame comprising an area for application of a unique identifier for a biological sample and a recess for irreversibly receiving a sample carrier; and
  ii) a sample carrier comprising a rigid frame adapted to fit within the cassette frame and to irreversibly engage therewith and a sample compartment for holding a biological sample defined by a bottom face and a top face, the sample carrier being adapted for irreversible engagement with the frame wherein the bottom face and top are dimensioned such that the top face and bottom face contact the sample so as to hold the sample in a fixed orientation relative to the sample carrier.

In a further aspect, the invention provides a method of handling a biological sample preparatory to a histology processing procedure comprising:
  i) placing a biological sample in a sample carrier comprising a compartment for holding a biological sample defined by a bottom face and a top face and a peripheral wall joining the two faces, both faces being transmissible to a processing fluid at a first location wherein the bottom face and top are dimensioned such that the top face and bottom face to hold the sample in a fixed orientation relative to the sample carrier;
  ii) recording data comprising a unique identifier associated with the sample on a receptacle and placing the sample carrier in the receptacle;
  iii) transporting the receptacle to a second location;
  iv) applying a unique identifier for the biological sample to a frame which comprises an area for application of the unique identifier and a recess for irreversibly receiving the sample carrier whereby the biological sample may be uniquely identified from the unique identifier on the frame;
  v) locating the sample carrier containing the biological in the frame to provide a histology processing assembly comprising the frame which bears the unique identifier for the sample and the sample carrier which contains the sample; and
  vi) processing the sample to produce a section having a pre-determined aspect for observation or analysis.

Preferably, the processing step vi) comprises subjecting the sample to known histological processing techniques to prepare the sample for slicing and slicing the sample to produce the section having the pre-determined aspect for observation or analysis. Where the sample carrier comprises a rigid frame, preferably the upper part of the sample carrier is removed prior to embedding the sample in processing wax and subsequent slicing of the fixed sample in the conventional manner using a microtome.

BRIEF DESCRIPTION OF THE FIGURES

The present invention is further described by way of example only with reference to the accompanying drawings, in which:

FIGS. 2A to 2C show a perspective view and FIGS. 2D and 2E show a perspective of a section of a histology processing assembly according to the invention;

DETAILED DESCRIPTION OF THE EMBODIMENTS

Figure 1A:
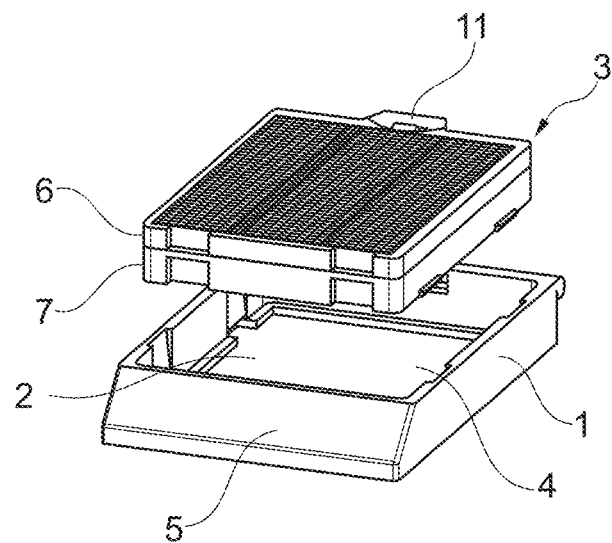
FIGS. 1A to 1C show a perspective view of the component parts of a histology processing assembly according to the invention having a rigid sample carrier and their initial and final configuration.
Figure 1B:
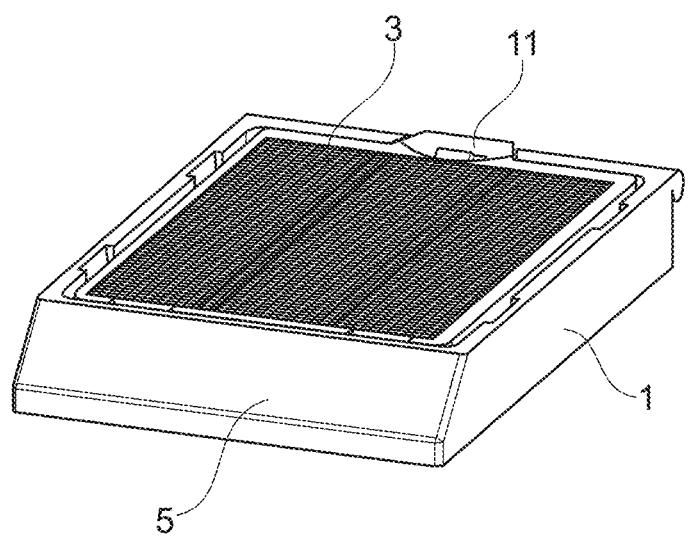
Figure 1C:
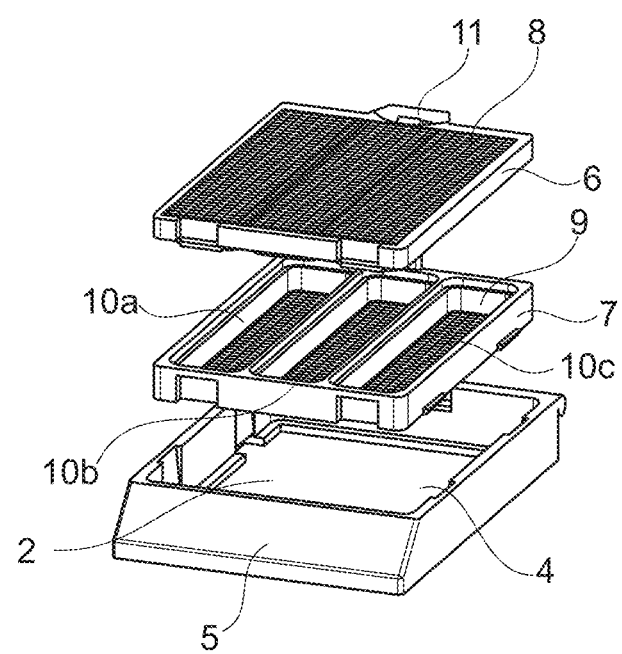

FIG. 1A shows a histology processing assembly having a cassette frame (1) with a recess (2) for receiving a rigid sample carrier (3). The bottom face of the cassette frame (1) has a bottom face (4), transmissible to processing fluids and radiation. As shown, this bottom face is open. It may however comprise a mesh, a rigid plastics sheet comprising apertures or other sheet which is transmissible to processing fluids. The cassette frame (1) has a sloping front wall (5) adapted to receive information enabling information associated with the sample to be analysed. The sample carrier (3) is made of a rigid plastics frame having an upper part (6) and a lower part (7) and is dimensioned to fit within recess (2) irreversibly as shown in FIG. 1B in a manual, snap-fit manner. The upper part (6) and lower part (7) have a mesh covering (8, 9), transmissible to processing fluids and radiation. Instead of a mesh covering the upper part and/or lower part may have a top face or a bottom face or both made of a plastics sheet having apertures defined therein. The sample carrier (3) has three sample recesses (10a, 10b, 10c) in a lengthways orientation. Fewer or greater sample recesses may be provided and may be lengthways, widthways or there may be multiple recesses along the length and across the width as desired. The upper part (6) and lower part (7) are adapted to fit together in a snap-fit manner. Whilst the sample carrier (3) is adapted to irreversibly fit into the recess (2), the upper part (6) is removal from the lower part (7) by means of lip (11), leaving the lower part (7) irreversibly fixed to the cassette frame (1).

Figure 2A:
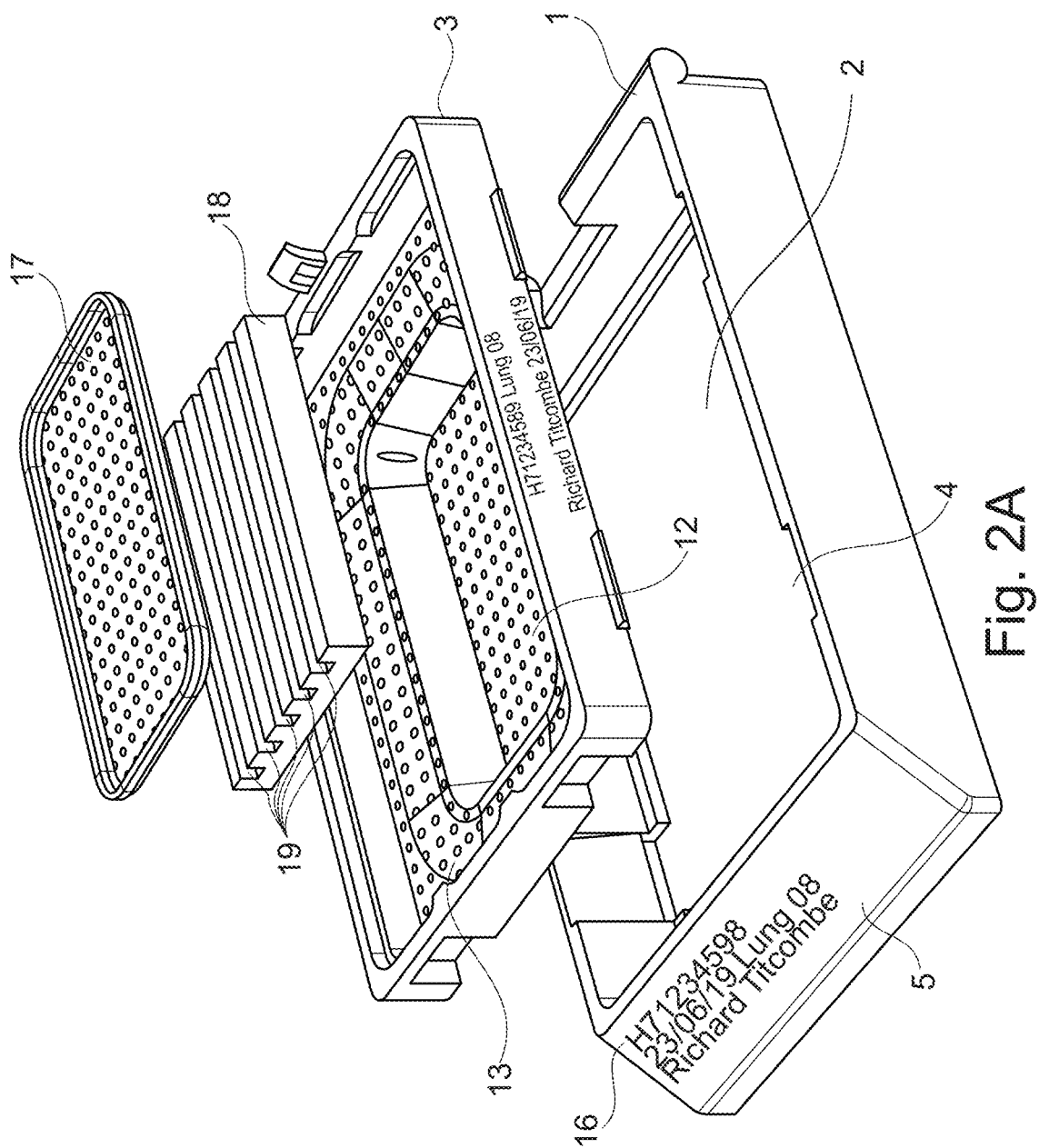
Figure 2B:
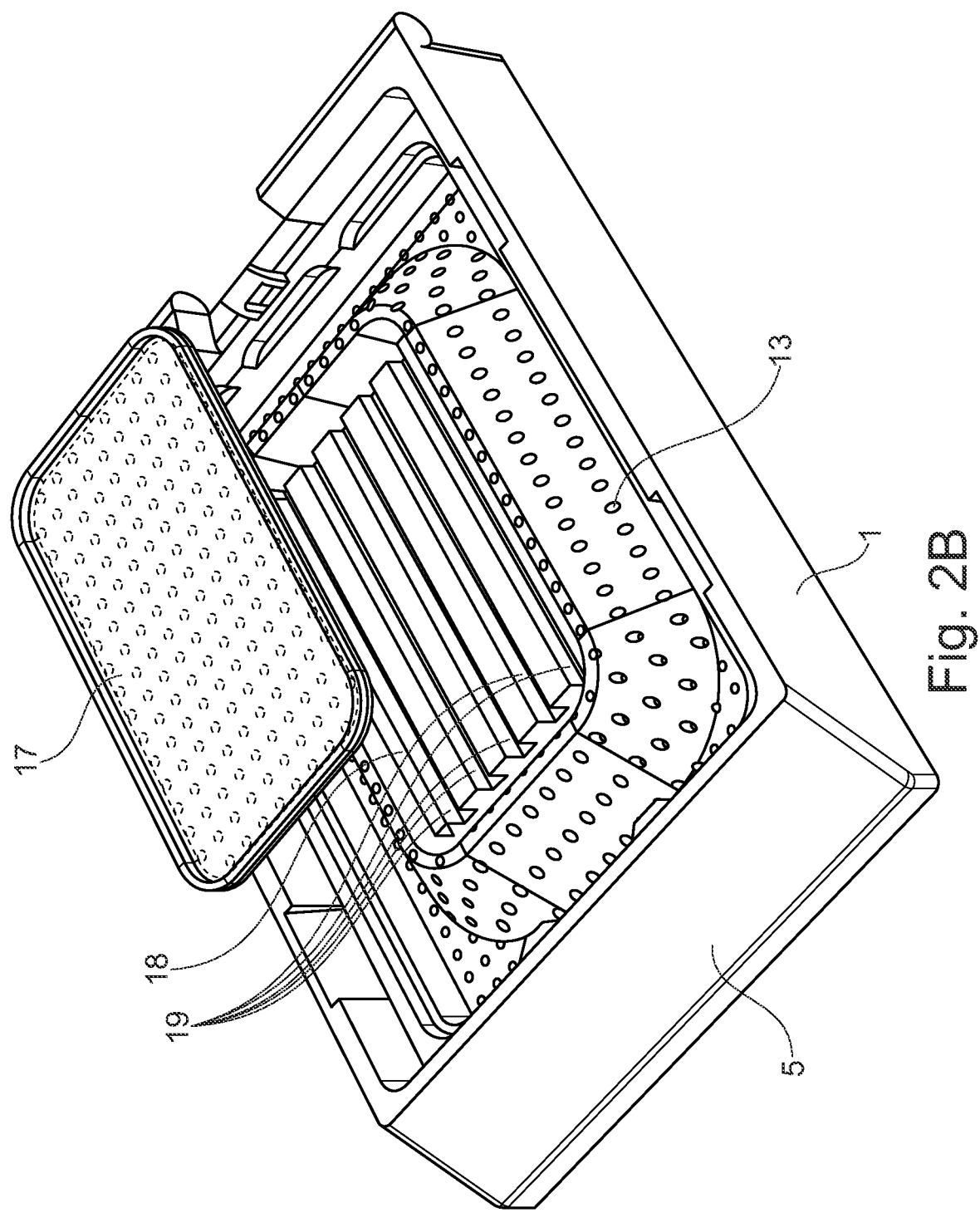
Figure 2C:
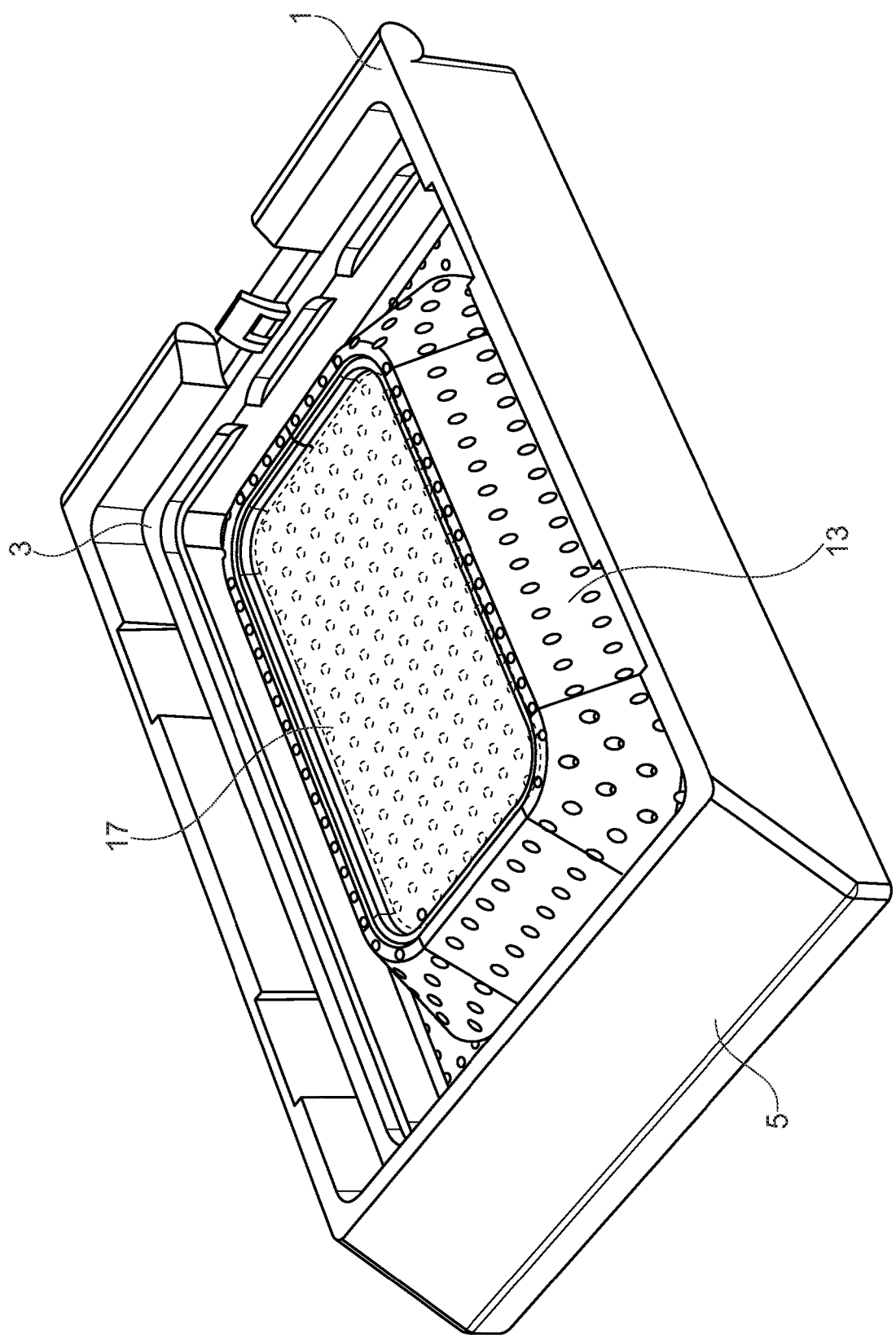

FIGS. 2A to 2E show a histology processing cassette according to the invention having a cassette frame (1) with a sloping front wall (5) adapted to receive information (16)

relating to the sample to be analysed. The sample carrier (3) comprises a rigid wall a sample compartment (12) and deformable peripheral portion (13), the sample carrier (3) being irreversibly engagable with the cassette frame (1). The sample carrier (3) is engageable in a manual, push-fit or snap-fit manner, with the cassette frame (1). The sample compartment (12) has a rectangular flexible bottom part and side walls (23) defining a depression and a top closure part (17) which is placed on top of the bottom part to form the enclosed sample compartment (12). The sample may be placed directly into the sample compartment (12) or may be placed in a sample pod (18) which is itself placed into the sample compartment (12). The sample pod (18) has multiple recesses (19), shown as longitudinal channels but which may be of any configuration and arrangement, each recess being adapted to receive a sample. The sample pod (18) is deformable or flexible and is placed in the sample compartment (12) of the sample carrier (3) as shown in FIG. 2B and the closure part (17) is placed over the sample compartment (12) as shown in FIG. 2C. The sample compartment (12) and sample pod (18) are dimensioned such that the sample is placed therein and is retained in a fixed orientation, thereby ensuring that the intended orientation for observation as determined by the clinician is retained as the sample carrier (3) is transported and placed in the cassette frame (1).

The sample carrier (3) is marked with information relating to the sample to be analysed. The sample is taken from the patient or subject or recovered from a stored location and placed in the sample carrier (3) which is marked with the sample information before, during or soon after the sample is placed therein. The sample carrier (3) containing the sample may then be placed in the cassette frame (1) which is also marked with the sample information or identifier. Thus, placing of the sample in the sample carrier (3) may be carried out at the same location or at a remote location to the cassette frame (1), and applying the sample information or identifier to both the cassette frame and to the sample carrier (3) enables sample tracing, control and pharmacovigilance between different locations for taking the same and analysing it.

The flexible portion (13) acts as a bridge between the sample compartment (12) and the rigid wall of sample carrier (3). The flexible portion (13) is configured so as to allow the sample compartment to be displaced between two stable positions, the first wholly within the recess of the cassette frame (1) such that it does not extend below or above the cassette frame (1) as shown in FIGS. 2B to 2D, and the second extending below the cassette frame as shown in FIG. 2E and being adapted to be displaced in a direction perpendicular to the plane defined by the rigid wall of the sample carrier.

Figure 2D:
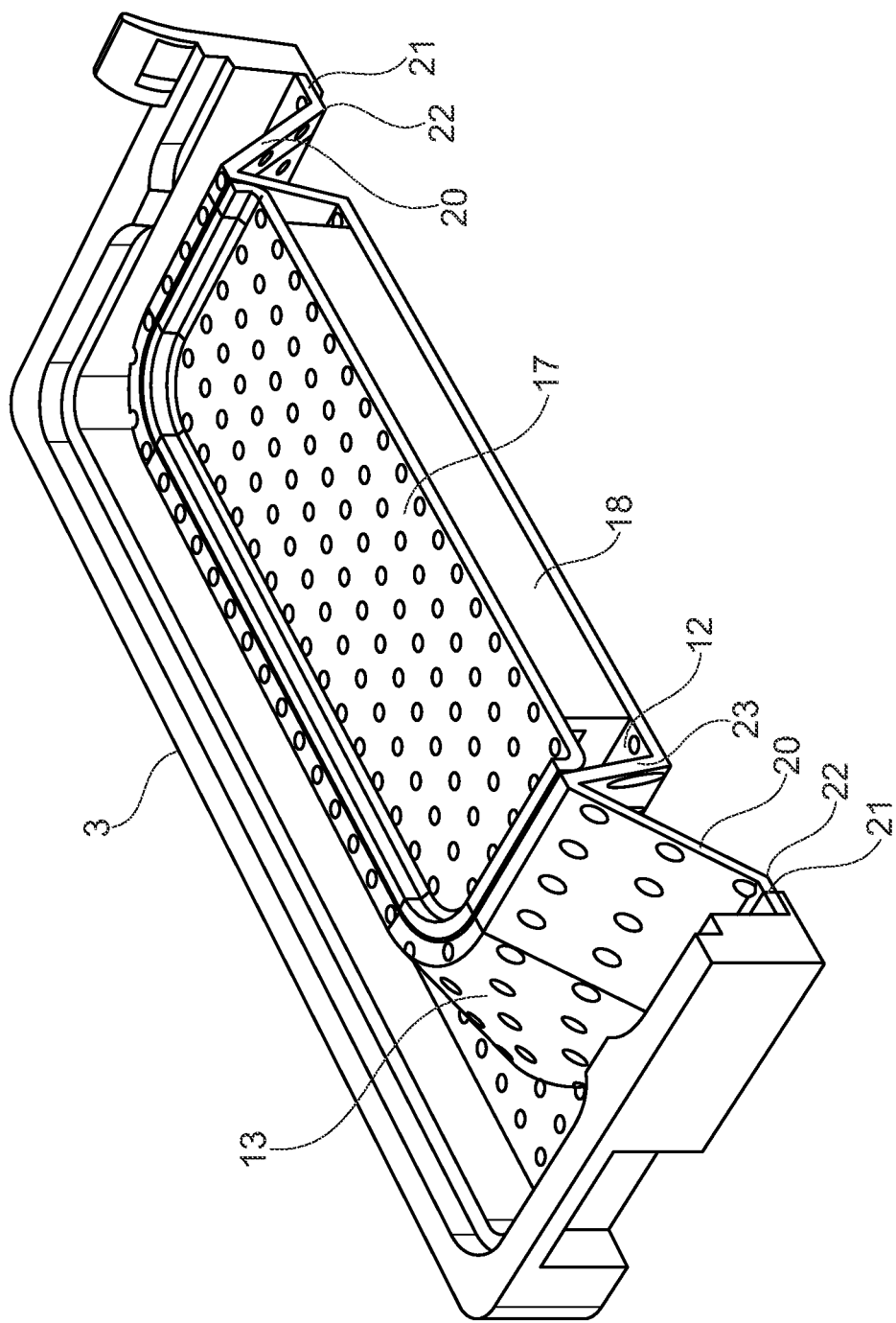

FIGS. 2D and 2E show perspective views of a longitudinal section of the processing cassette in the first position shown in FIG. 2D and the second position, shown in FIG. 2E. The peripherally extending flexible portion (13) comprises an inner portion (20) and an outer portion (21) connected via a hinge or crease (22), the inner and outer portions and hinge extending peripherally around the sample compartment (12) and, together, constituting flexible portion (13). In the first position, the inner portion slopes upwardly towards the sample compartment (12) as shown in FIG. 3D and in the second position the inner portion slopes downwardly towards the sample compartment (12) as shown in FIG. 2E.

The sample compartment (12) may be displaced between the first position and the second position, manually or by automated means. In the second position, the sample compartment (12) and, if present, sample pod (18) are proud of the bottom face of the cassette frame and may be subjected to histology or pathology procedures, for example sectioning. The sample compartment (12) and pod (18) are suitably constructed of sectionable material.

Figure 3A:
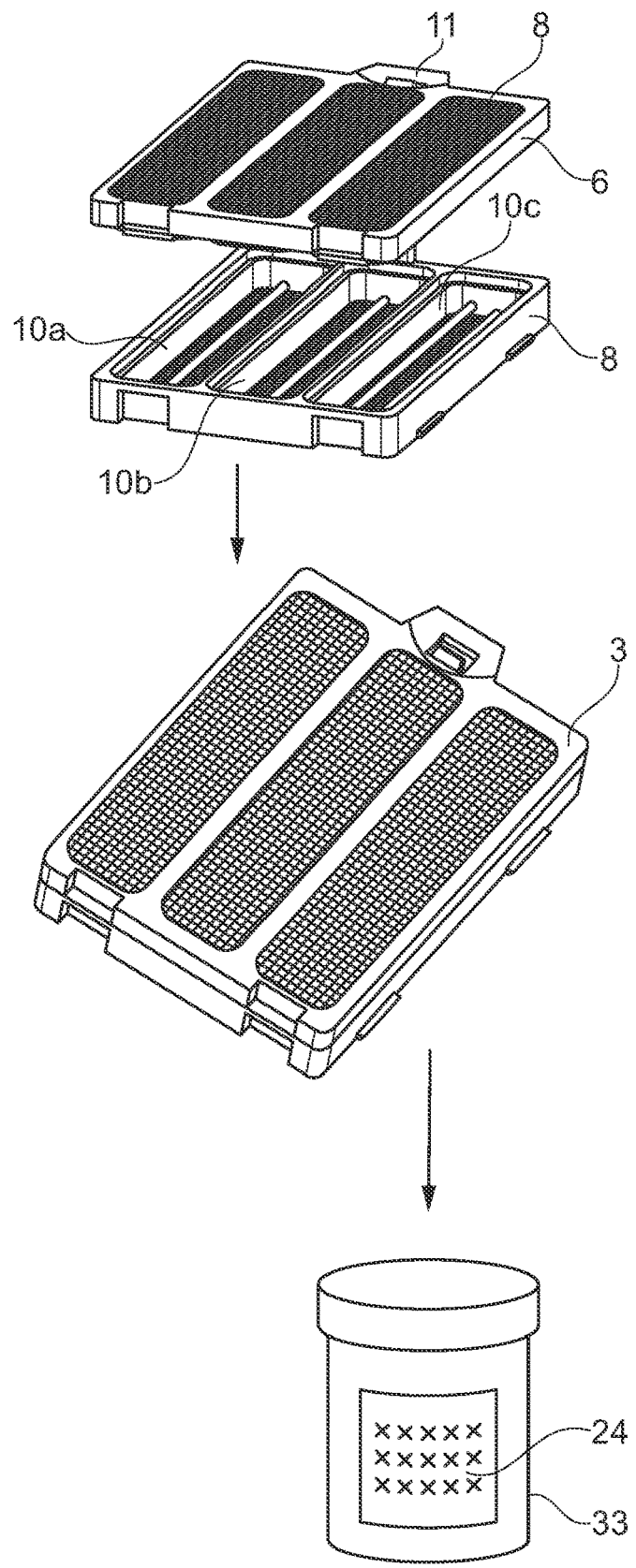
FIGS. 3A to 3C show a schematic representation of a process according to the invention.
Figure 3B:
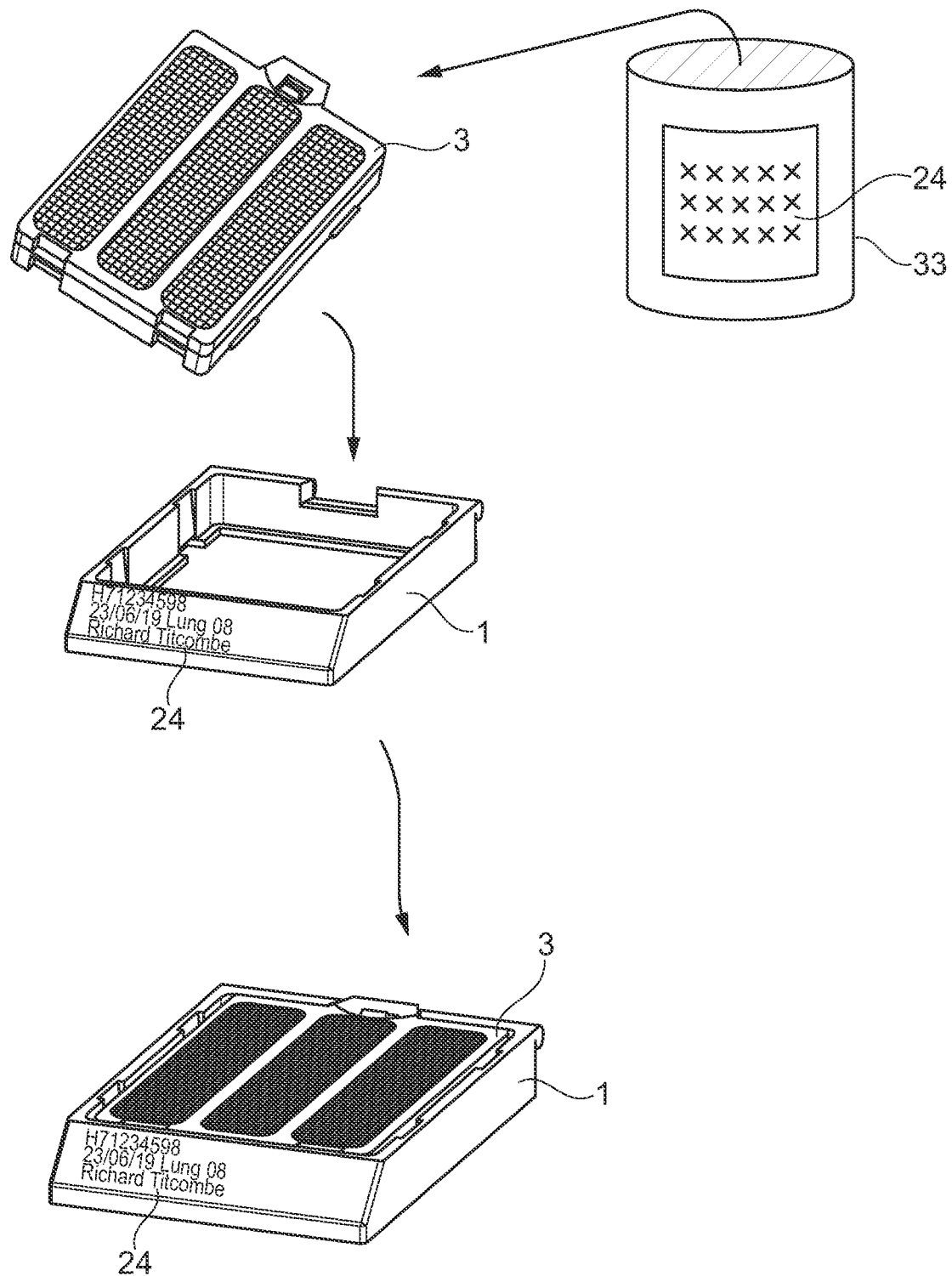
Figure 3C:
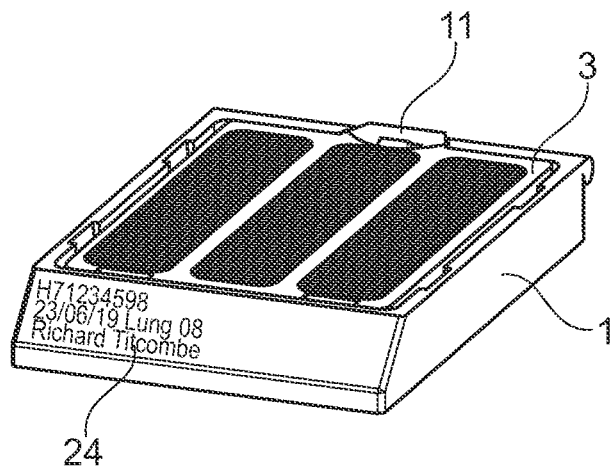
Figure 3C:
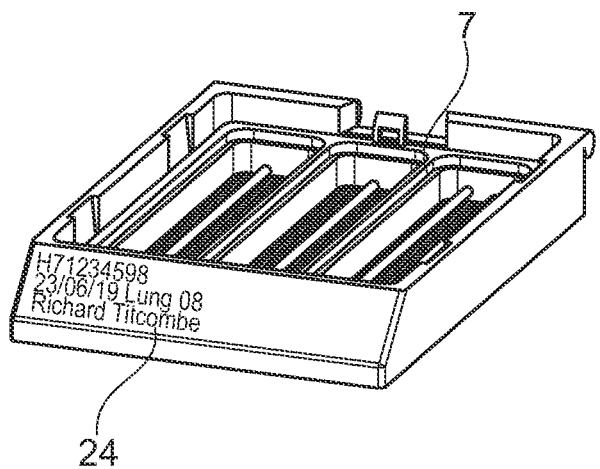

FIGS. 3A to 3C illustrate the method of the invention in that the sample, biopsy or specimen is obtained from the patient or retrieved from a stored location and placed in the sample compartment (12) of the sample carrier (3) as shown in FIG. 3A-I. The sample compartment is securely closed as shown in FIG. 3A-II. The upper part (6) is placed over the lower part to provide a closed sample carrier (3. The closed sample carrier is then placed in a sample pot (23) in FIG. 3A-III marked with information (24) relating to the patient. This process may be carried out in a clinic.

The pot (23) and optionally the sample carrier (3) are marked with information or an identifier for the sample(s). The pot (3) may then be transported to a remote location where the sample carrier (3), with the samples retained in a fixed orientation therein, may then be processed in a laboratory process.

As shown in FIG. 3B, in a laboratory process, the pot (23) is received from a remote location, for example a clinic or hospital, (FIG. 3B-I) the sample carrier (3) is removed from pot (23) (FIG. 3B-II) and irreversibly placed in a cassette frame (1) as shown in FIG. 3B-III, marked with the sample information or identifier, for example by printing, such that the sample(s) is in the desired orientation for subsequent processing and sectioning. The sample carrier is located within the height of the wall of the cassette frame such that it does not protrude above or below the wall of the cassette frame. The information may be obtained directly from the pot (23) or by an automated system. After sample processing, for example subjecting to contact with histological processing fluids, the upper part (6) of the sample carrier (3) is discarded and the sample may then be embedded in wax in a known manner in a known histological sample preparation and analysis process and subjected to further processing.

The sample may then be processed as shown in FIG. 3C-I by removing the top (6) of the sample carrier (3) to expose the samples in each of the channels in the sample compartment. The samples are then suitably embedded in a standard histological process or processed in another desired manner. The sample is thereby embedded in the desired orientation determined by the clinician on taking the sample in the clinic. The orientation and handling of the sample has been carried out remotely from the analysis process with no physical handling of the sample since the initial placing of the sample in the sample carrier, thereby reducing the risk of sample damage or otherwise being compromised.

Figure 4A:
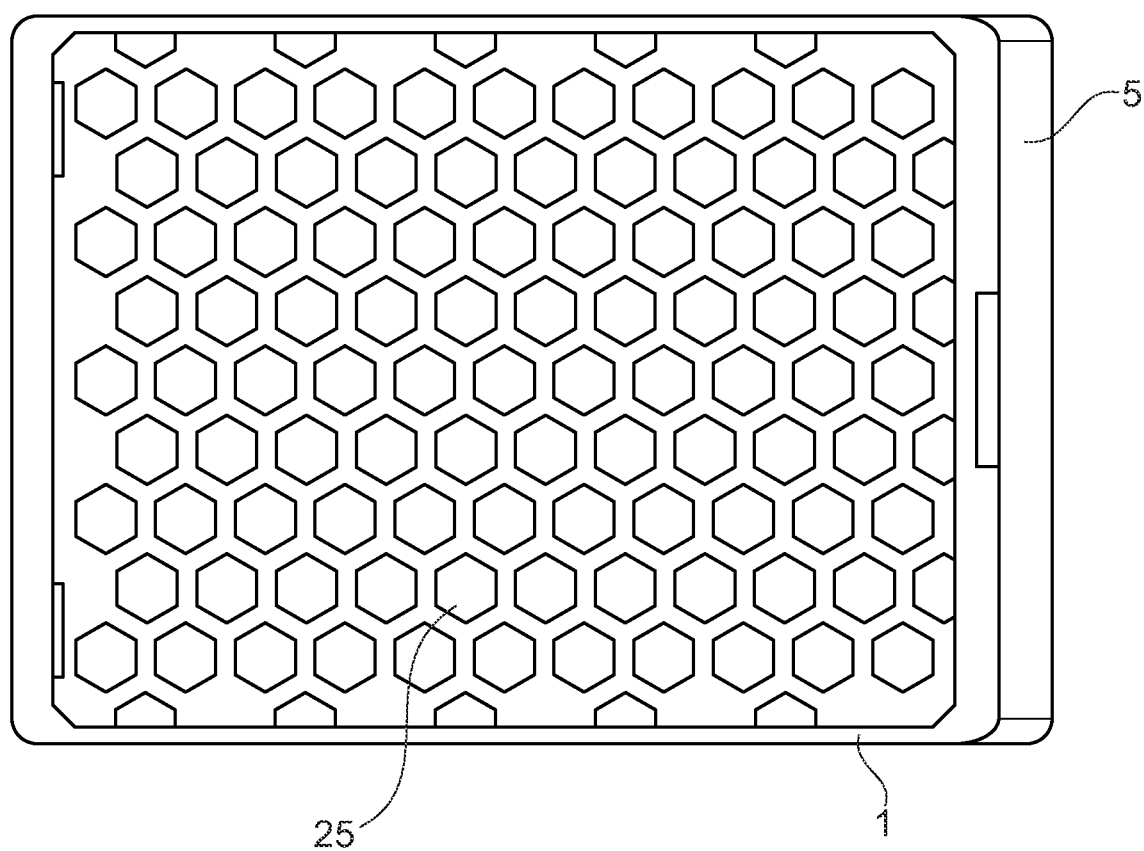
FIGS. 4A and 4B show a cassette frame and a top face covering for the cassette frame or for the sample carrier, for use in the invention.
Figure 4B:
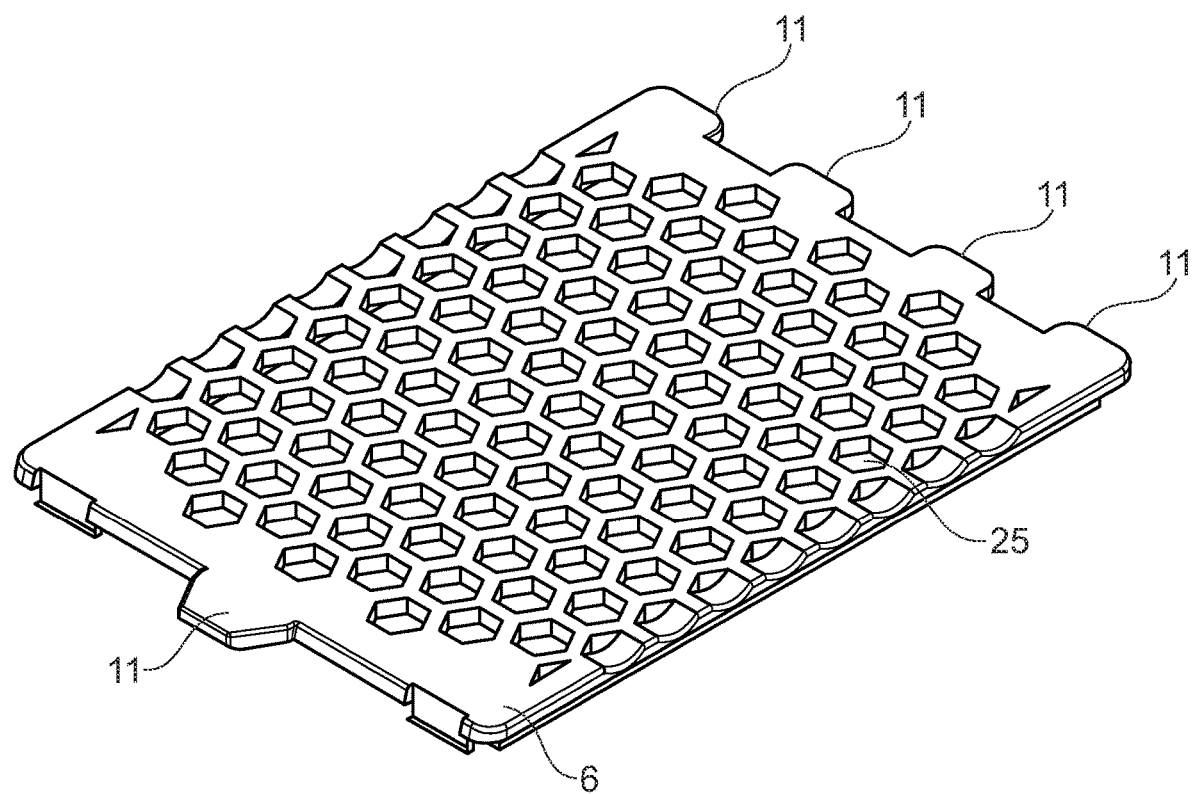

FIG. 4A shows a cassette frame for use in the invention which has a bottom face (4) defined by a rigid plastics sheet having apertures (25) therein in a regular array. FIG. 4B shows a planar detachable top part of a sample carrier. This may be employed instead of a top part having a mesh and is removable from the lower part of the sample carrier to enable sample processing as shown in FIG. 3C.

If desired, the cassette frame may comprise a lid s shown in FIG. 4B for detachable or pivotal engagement with the cassette frame.

The invention claimed is:

1. A histology processing assembly comprising:
 i) a cassette frame comprising a recess for irreversibly receiving a sample carrier; and
 ii) the sample carrier comprising a rigid frame and an apertured bottom face and an apertured top face which together define a sample compartment for holding a biological sample and which carrier is transmissible to processing fluids and/or radiation, the rigid frame of the sample carrier and the cassette frame comprising complementary engaging means for irreversible engagement of the closed sample carrier with the said cassette frame.

2. An assembly according to claim 1 wherein the sample carrier comprises:
   i) the rigid frame defining the sample compartment, wherein the rigid frame is configured for insertion into and engagement with the cassette frame wherein the sample carrier and cassette frame are dimensioned such that the top face of the sample carrier is flush with a plane defined by a top edge of the cassette frame when the sample carrier is irreversibly located in the cassette frame; or
   ii) the rigid frame and a flexible sample holder comprising a sample compartment and a flexible portion configured for insertion into and engagement with the cassette frame.

3. An assembly according to claim 2 wherein the said rigid frame comprises comprising four walls.

4. An assembly according to claim 3 wherein the rigid frame comprises a single part defining a rigid wall or comprises an upper part and a lower part adapted to engage together to form the rigid frame.

5. An assembly according to claim 2 wherein the said sample carrier comprises the sample compartment and the flexible portion is located around at least part of a periphery of the sample compartment to act as a bridge between the sample compartment and the rigid frame.

6. An assembly according to claim 5 wherein the flexible portion is configured so as to allow the sample compartment to be located in two stable positions by displacement in a direction perpendicular to the plane of the rigid frame.

7. An assembly according to claim 6 wherein the flexible portion comprises an outer part connectable to or connected to the rigid frame and an inner part which connects to the sample compartment to form a bridge between the sample compartment and the rigid frame.

8. An assembly according to claim 7 wherein the inner part and outer part are hingedly connected such that the inner part is adapted to extend at an inclined angle relative to the plane of the rigid frame of the sample carrier in a first configuration and at an inclined angle on the opposite side of the plane in a second configuration thereby enabling the sample compartment to be locatable in a stable first and second position by application of force to displace the sample compartment perpendicularly relative to the plane of the rigid frame.

9. An assembly according to claim 5 wherein the sample carrier is adapted to receive or comprises a sample chip having one or more sample bays formed in one face thereof for receipt of the samples.

10. An assembly according to claim 9 wherein the sample chip comprises a plurality of sample bays extending along a length of the chip as linear, parallel channels.

11. An assembly according to claim 1 in which the top face and/or and or the bottom face comprises
   i) a mesh sheet across the bottom face and a mesh sheet across the top face, the mesh sheets defining the said apertures; or
   ii) a rigid plastics sheet having apertures formed therein.

12. An assembly according to claim 11 comprising a hingedly mounted or removable lid comprising a mesh screen to define the said top face.

13. An assembly according to claim 1 wherein the complementary engaging means comprises a retaining lug on the sample carrier adapted to engage with top walls of the cassette frame to prevent the sample carrier passing through the cassette frame, engagement lugs on the sample carrier and corresponding recesses in the walls of the cassette frame, and a retaining flange extending inwardly from the bottom of the cassette frame walls configured for the engagement lugs to irreversibly engage with an underside of the cassette frame walls thereby to preclude further movement of the sample carrier relative to the cassette frame.

14. An assembly according to claim 1 wherein the cassette frame comprises two side walls, a back wall and a front wall and optionally a bottom face defining a recess for receiving the sample carrier, the front wall comprising an area for receiving a unique identifier such that upon insertion of the sample carrier in the recess, a unique identifier for the sample in the carrier is applied to the area for receiving the identifier.

15. An assembly according to claim 1 wherein the cassette frame is of the same shape as a standard histology processing cassette and of dimensions:
   i) 28 to 32 mm×25 to 28 mm×5 to 10 mm; or
   ii) 50 to 55 by 65 to 80 by 12 to 17 mm.

16. An assembly according to claim 1 wherein the sample carrier fits in the cassette frame snugly.

17. An assembly according to claim 16 wherein the sample carrier and/or cassette frame comprises engagement means such that the sample carrier clips into the cassette frame.

18. A method of handling a biological sample preparatory to a histology processing procedure comprising:
   i) placing a biological sample in a sample carrier comprising a compartment for holding a biological sample at a first location;
   ii) placing the sample carrier in a receptacle and recording data comprising a unique identifier associated with the sample on the receptacle;
   iii) transporting the receptacle to a second location; and
   iii)
   iv) removing the sample carrier from the receptacle and irreversibly locating the sample carrier containing the biological sample in a cassette frame to provide a histology processing assembly comprising the cassette frame and the sample carrier which contains the sample.

* * * * *